United States Patent
Krivoruchko et al.

(10) Patent No.: US 7,356,903 B2
(45) Date of Patent: Apr. 15, 2008

(54) STENT DELIVERY SYSTEM

(75) Inventors: Mike Krivoruchko, Forestville, CA (US); William Berthiaume, Santa Rosa, CA (US); Don Tran, Windsor, CA (US); Kris Kristoffersen, Santa Rosa, CA (US); Erik Griswold, Santa Rosa, CA (US); Vance Swanson, Santa Rosa, CA (US); Somboune Singkeo, Santa Rosa, CA (US); Fertac Bilge, Santa Rosa, CA (US); Sean Miller, Santa Rosa, CA (US)

(73) Assignee: Medtronic Vascular, Inc., Sanata Rosa, CA (US)

( * ) Notice: Subject to any disclaimer, the term of this patent is extended or adjusted under 35 U.S.C. 154(b) by 500 days.

(21) Appl. No.: 10/903,757

(22) Filed: Jul. 30, 2004

(65) Prior Publication Data
US 2005/0027306 A1   Feb. 3, 2005

Related U.S. Application Data

(62) Division of application No. 09/691,650, filed on Oct. 17, 2000, now Pat. No. 6,786,918.

(51) Int. Cl.
*B23P 11/02* (2006.01)
*B21D 39/00* (2006.01)
*B25B 27/14* (2006.01)
*A61F 2/06* (2006.01)

(52) U.S. Cl. ............... 29/446; 29/451; 29/505; 29/272; 29/515; 623/1.11; 623/1.15

(58) Field of Classification Search ............... 29/445, 29/446, 450, 451, 452, 272, 281.5, 283.5, 29/525, 505, 515; 623/1.11, 1.12, 1.15, 1.16
See application file for complete search history.

(56) References Cited

U.S. PATENT DOCUMENTS 4,665,918 A     5/1987  Garza et al.
4,705,517 A  * 11/1987  DiPisa, Jr. ............... 606/158

(Continued)

FOREIGN PATENT DOCUMENTS

EP          1025813        8/2000

(Continued)

*Primary Examiner*—David P. Bryant
*Assistant Examiner*—Christopher M Koehler

(57) ABSTRACT

The present invention is a device for delivering a self-expanding stent. The device has an inner shaft and an outer shaft moveable with respect to the inner shaft. The self expanding stent is received on the inner shaft adjacent its distal end. A tapered tip is located on the inner shaft distal end and it forms a smooth transition from the delivery device to the guide wire extending therethrough. A handle allows the practitioner to deploy the stent single handedly. The stent may have its segments in a first radial configuration for deliver of the stent or the stent may have a plurality of segments in a first radial configuration and a plurality of second segments in a second radial position.

13 Claims, 8 Drawing Sheets

U.S. PATENT DOCUMENTS

| | | |
|---|---|---|
| 5,284,475 A | 2/1994 | Mackal |
| 5,328,469 A | 7/1994 | Coletti |
| 5,344,426 A * | 9/1994 | Lau et al. ................. 623/1.11 |
| 5,391,172 A | 2/1995 | Williams et al. |
| 5,466,230 A | 11/1995 | Davila |
| 5,484,444 A | 1/1996 | Braunschweiler et al. |
| 5,593,394 A | 1/1997 | Kanesaka et al. |
| 5,645,559 A | 7/1997 | Hachtman et al. |
| 5,683,451 A * | 11/1997 | Lenker et al. ............. 623/1.11 |
| 5,688,234 A | 11/1997 | Frisbie |
| 5,782,855 A | 7/1998 | Lau et al. |
| 5,843,090 A | 12/1998 | Schuetz |
| 5,957,929 A * | 9/1999 | Brenneman ............... 623/1.11 |
| 5,980,533 A | 11/1999 | Holman |
| 6,001,123 A * | 12/1999 | Lau .......................... 623/1.12 |
| 6,036,682 A | 3/2000 | Lange et al. |
| 6,071,287 A * | 6/2000 | Verbeek .................... 623/1.11 |
| 6,146,416 A * | 11/2000 | Andersen et al. .......... 623/1.15 |
| 6,221,057 B1 | 4/2001 | Schwartz et al. |
| 6,254,628 B1 * | 7/2001 | Wallace et al. ............ 623/1.12 |
| 6,395,017 B1 | 5/2002 | Dwyer et al. |

FOREIGN PATENT DOCUMENTS

| | | |
|---|---|---|
| WO | WO98/07390 | 2/1998 |
| WO | WO 99/49808 | 10/1999 |

* cited by examiner

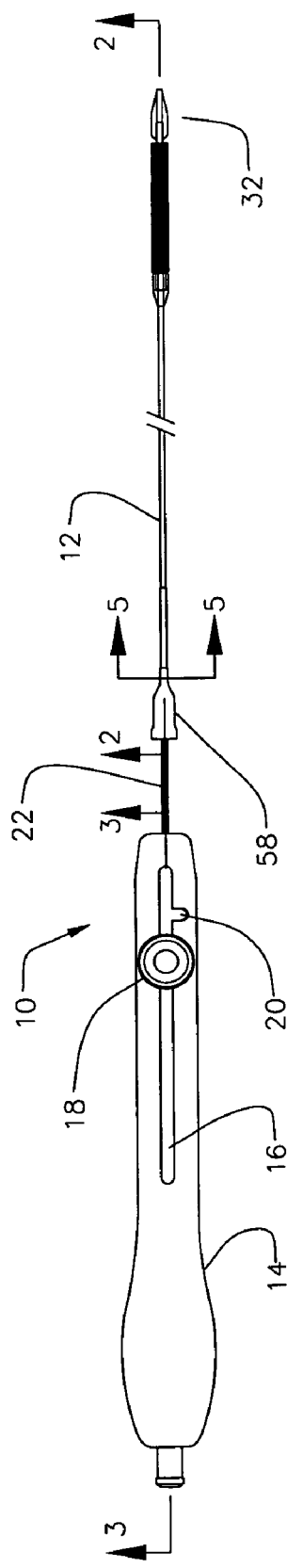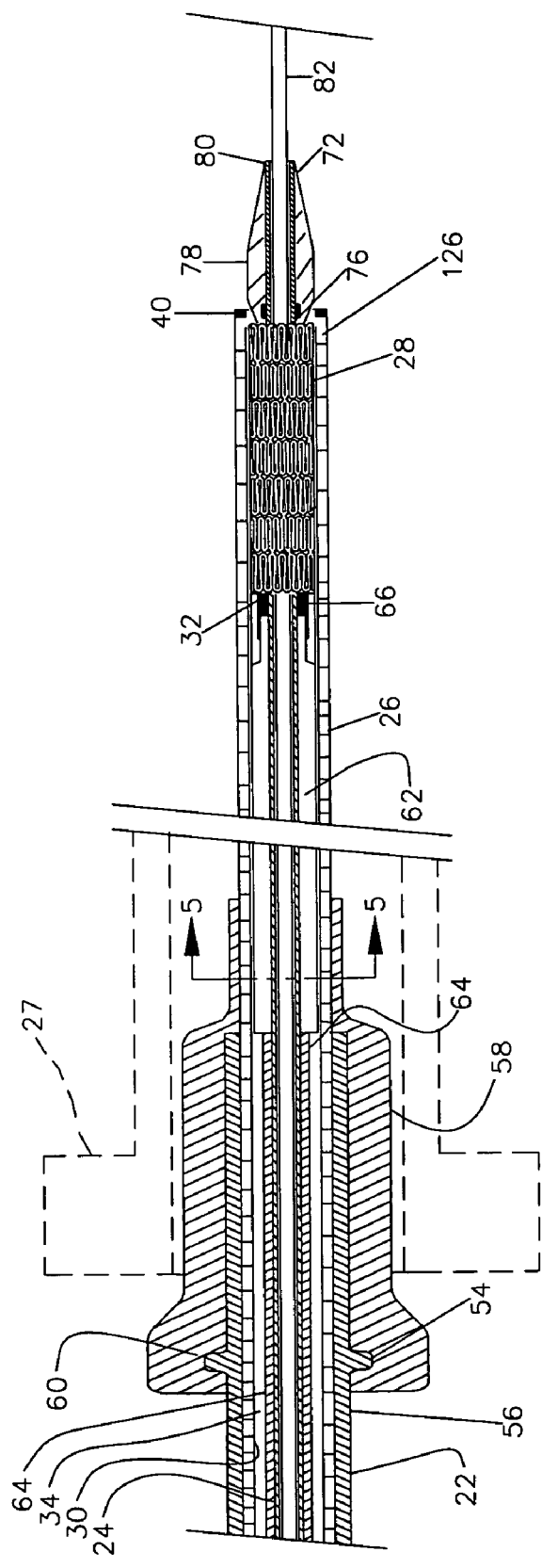

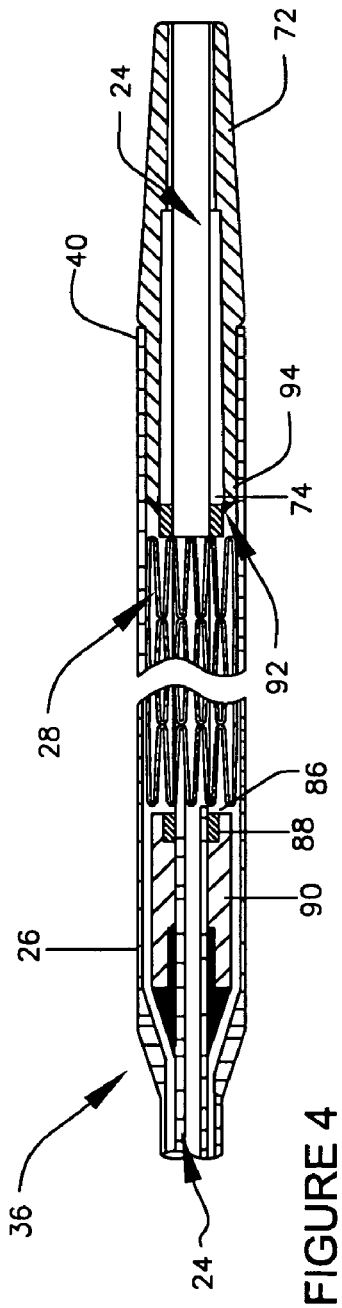
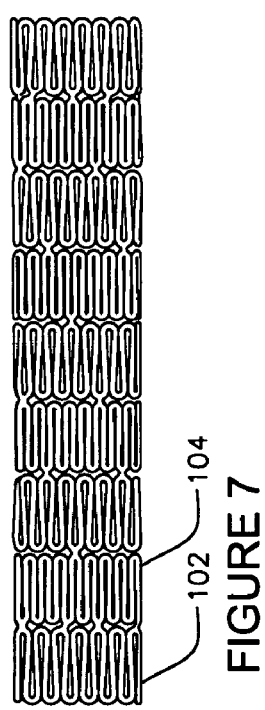
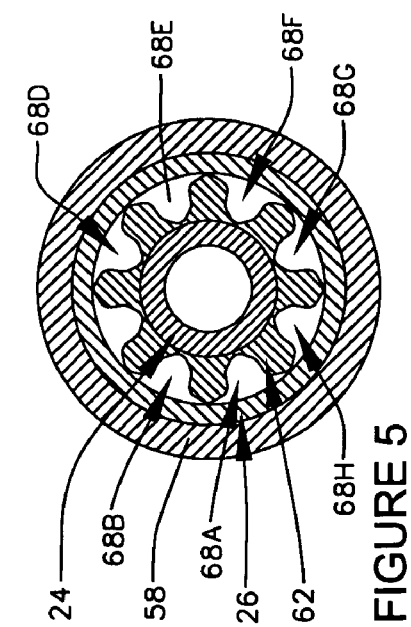
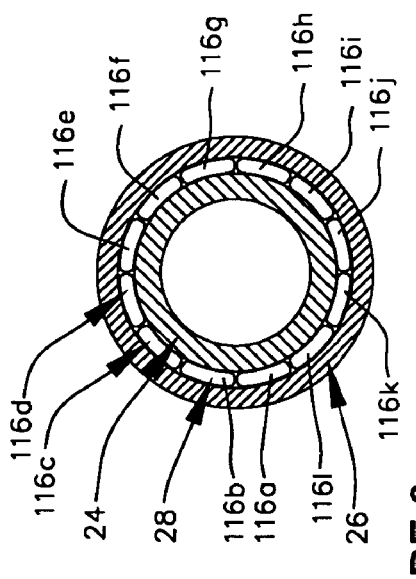
FIGURE 4
FIGURE 7
FIGURE 5
FIGURE 6
FIGURE 8

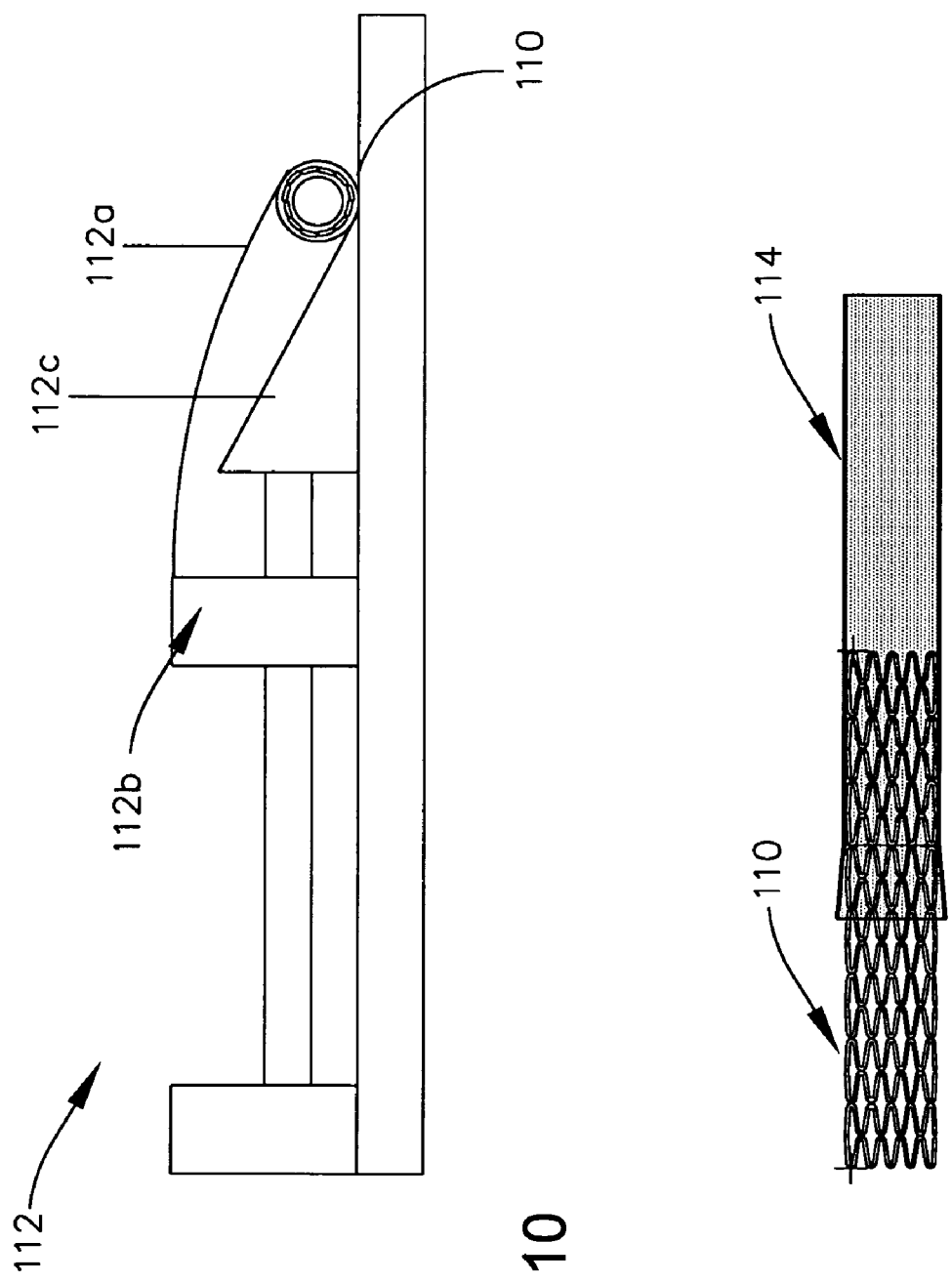

STENT DELIVERY SYSTEM

RELATED APPLICATIONS

This application is a divisional of and claims priority from U.S. patent application Ser. No. 09/691,650 filed Oct. 17, 2000, now U.S. Patent No. 6,786,918, issued on Sep. 7, 2004.

FIELD OF THE INVENTION

The present invention relates generally to methods and devices for delivering and deploying a medical endoprosthesis, and more particularly to a delivery system for a self-expanding endoprosthesis.

BACKGROUND OF THE INVENTION

Medical endoprostheses, commonly referred to as stents, are known in the prior art for maintaining the patency of a diseased or weakened vessel or other passageway. Stents have been implanted in various body passageways such as blood vessels, the urinary tract, the biliary tract, and other body lumens. These devices are inserted into the vessel, positioned across the treatment area and then expanded or allowed to self expand to keep the vessel or passageway open. Effectively, the stent overcomes the natural tendency of the weakened area to close. Stents used in the vascular system are generally implanted transluminally during or following percutaneous transluminal angioplasty.

Self expanding stents may be mechanically compressed springs which expand when released, and/or they may be constructed from shape-memory materials including shape memory polymers and metals such a nickel-titanium (Nitinol) alloys and the like which have shape-memory characteristics.

Delivery devices for self expanding stents have included a protective sheath to prevent premature expansion at body temperatures for heat induced shape memory devices or to contain mechanically restrained or stress induced shape memory devices. The sheath also enhances the delivery through the tortuous vessels of the vascular system. Such sheaths increase the profile of the delivery system, necessitating use of a delivery catheter with a large diameter. The large diameter of the delivery catheter may in turn increase the risk of complications at the patient access site.

The increased profile also detracts from the ability of the device to navigate through tortuous vessels or passageways. The increased cross-sectional profile of the delivery system may make it impossible to deliver a self expanding stent to the treatment area and may decrease the ability to deliver sufficient contrast material through the guide catheter for enabling precise positioning.

In addition to the large profile of the delivery system, another problem associated with self expanding stents is that the stent itself cannot be radially compressed to a low profile. Since most such stents are cut from a tubular member, they are limited to the radial size of the tube from which they were cut. As explained above, it is desirable to keep the profile of the stent as small as possible. Furthermore, deploying a self expanding stent requires manipulating the outer sheath while keeping the stent carrying shaft stationary in order to properly place the stent at the treatment site.

In the event that a distal protection device is being used during the vascular procedure, the present invention can be used for retrieving the distal protection device. Distal protection devices are delivered via a guidewire and are positioned distal of the treatment area where they are expanded across the vessel to capture emboli that may escape during the procedure or placement of the stent. These devices are often self expanding and thus deployed and retrieved with a sheath. The procedure can become very time consuming if the delivery system must be completely removed after the procedure and then the distal protection device sheath be reinserted to withdraw the catheter. Thus, it would be an advantage to use the delivery device as the retrieval device for the distal protection device. Therefore, what is needed is a delivery system that addresses the problem of compressing the self expanding stent to a lower profile than that achieved with conventional stent delivery systems. A stent delivery system that is easy to manipulate, has a low profile and can also accommodate a distal protection device is also needed.

SUMMARY OF THE INVENTION

The present invention is a delivery system for a self expanding stent that has catheter with an outer shaft moveable with respect to an inner shaft for releasing a stent. The stent is positioned on the inner shaft and restrained by the outer shaft until it is released at the treatment site. The catheter tip is mounted on the inner shaft and is tapered to provide a smooth transition from the catheter outer shaft to the guidewire extending distally of the delivery system. A handle is located on the proximal end for one-handed operation when deploying the stent.

The system may include a valve relief that is selectively coupled to the catheter. By coupling the valve relief to the hemostatic valve or tuohy-borst coupler, the catheter can be moved within the hemostatic valve while reducing back bleed.

The catheter may deploy a stent retained in one of two configurations. In the first configuration, all the stent segments are compressed together and have the same radial position about the inner shaft. In the second configuration, certain crowns of the stent segments are positioned within the other crowns of the stent segments such that some have a first radial position and some have a second radial position. The second position is achieved by pressing certain crowns of segments inward after the first stent roll down to the first position when all the segments have the same radial position.

In alternative embodiments of the delivery system, the catheter outer shaft may extend past the inner shaft. This creates an area within the delivery system for retrieving a distal protection device. Alternatively, the inner shaft can be withdrawn sufficiently within the outer shaft to create an area to accommodate a distal protection device for retrieval with the delivery system catheter.

BRIEF DESCRIPTION OF DRAWINGS

For a more complete understanding of the features, aspects, and advantages of the present invention, reference is now made to the following description, appended claims, and accompanying drawings wherein:

FIG. 1 is a side elevational view of the delivery system of the present invention;

FIG. 2 is a cross-sectional view of the distal portion of the delivery system of the present invention taken along lines 2-2 of FIG. 1;

FIG. 4 is a cross-section of an alternative embodiment of the distal end of the delivery system of the present invention;

FIG. 5 is a cross-sectional view taken along 5-5 of FIG. 1;

FIG. 6 is a side view of one embodiment of a self expanding stent;

FIG. 7 is a side view of an alternative embodiment of a self-expanding stent;

FIG. 8 is a cross sectional view of a reduced stent in a first configuration;

FIG. 10 is a schematic of the initial stent roll down fixture;

FIG. 11 is a schematic of placing an initially rolled down stent in a tubing;

DETAILED DESCRIPTION OF THE PREFERRED EMBODIMENTS

Figure 3:
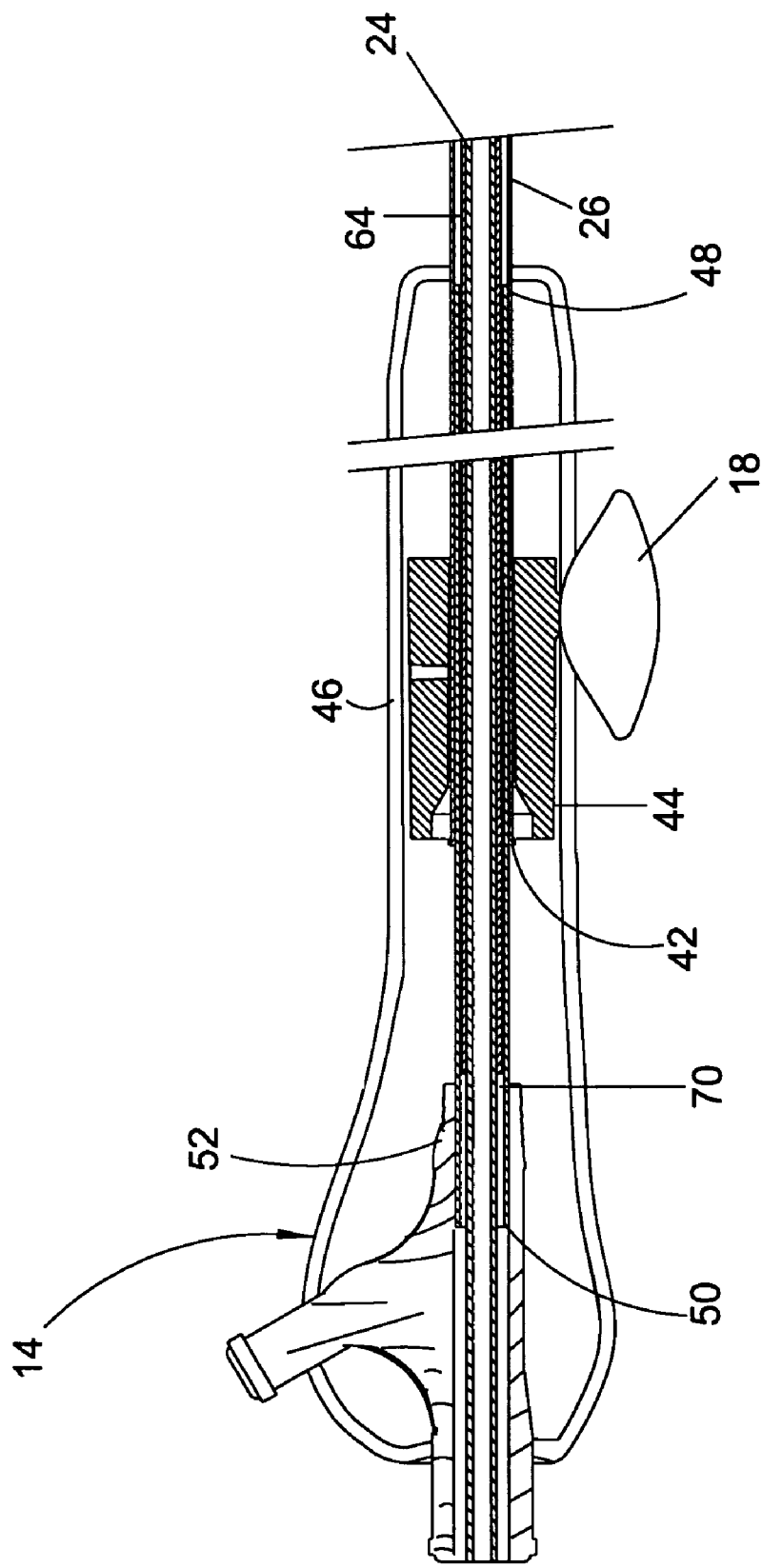
FIG. 3 is a cross-sectional view of the proximal portion of the delivery system of the present invention taken along line 3-3 of FIG. 1.

The present invention is a system for delivering a self expanding stent. Stent delivery system, designated 10 in FIG. 1, consists of an elongated member 12 and a handle 14. Handle 14 includes a longitudinal slot 16 along which knob 18 can reciprocate. A transverse slot 20 is located at the distal end of longitudinal slot 16 and knob 18 can rotate and enter transverse slot 20. A strain relief 22 is located at handle 14 distal end and surrounds the proximal exterior of elongated member 12 to provide a smooth transition between handle 14 and elongated member 12.

Turning now to FIGS. 2 and 3, elongated member 12 comprises an inner shaft 24 and an outer shaft 26. The outer shaft 26 is moveable with respect to the inner shaft 24 for releasing stent 28 at the desired treatment site. Outer shaft 26 is preferably a braided composite consisting of a nylon outer jacket, a stainless steel wire braid and a polyether block amide inner layer. Outer shaft 26 inner lumen surface 30 is preferably coated, such as with silicone, to reduce friction between the inner and outer shaft 26 during deployment of stent 28. Inner shaft 24 is preferably made of a composite material such as a stainless steel braid fully encapsulated in a polyimide/FEP blend. Stent 28 is positioned on inner shaft 24 at the distal portion 32 of the elongated member 12 and is preferably a self expanding stent 28 made from a shape memory material such as nitinol or a mechanically compressible spring material. Outer shaft lumen 34 has preferably a substantially constant diameter along the length as shown in FIG. 2, although its distal portion can be enlarged or reduced, depending upon the size of the stent, to accommodate the stent within the delivery system 10. Accordingly, distal portion 36 of outer shaft 26 has an enlarged inner lumen diameter to accommodate the stent 28 as seen in FIG. 4. A radiopaque marker 40 is located on outer shaft distal end. Radiopaque marker 40 enables the practitioner to view the outer shaft 26 position during the procedure.

As shown in FIG. 3, proximal end 42 of outer shaft 26 is secured to a slider 44 of handle 14. Slider 44 is positioned within handle housing 46 and is moveable on a hypotube shaft 48 extending from distal end of handle 14 through handle housing 46. Proximal end 50 of hypotube shaft 48 is secured to a luer fitting 52. Luer fitting 52 can be any suitable luer fitting, such as a two arm luer as shown in FIG. 3 or a one arm luer as shown in FIG. 1. Knob 18 extends from the exterior of handle housing 46 though longitudinal slot 16 into handle housing interior where it is coupled to slider 44. When the practitioner manipulates knob 18 along longitudinal slot 16 during deployment of the stent, outer shaft 26 moves with respect to inner shaft 24. Knob 18 and slider 44 are rotatably moveable on hypotube shaft 48. When knob 18 is rotated and positioned in transverse slot 20, it cannot translate along longitudinal slot 16 and in turn the outer shaft 26 cannot move longitudinally. Accordingly, the device is in a locked position preventing unintended deployment of stent 28.

Strain relief 22 includes a raised ring 54 approximate its distal end 56. Annular valve relief 58 is positioned around the outer shaft 26 and has an inner groove 60 for receiving raised ring 54 therein for releasably securing valve relief 58 to strain relief 22. Valve relief 58 allows the practitioner to selectively close the hemostatic valve or tuohy-borst coupler (together with an introducer collectively represented by the dashed line element 27) about valve relief 58, reducing back bleed while permitting free movement of the delivery system 10 during the procedure.

The inner shaft 24 includes an elongated tubular channel spacer 62 and a tubular spacer 64 and extends from the delivery system distal portion 32 through hypotube shaft 48 in handle 14 to secure at luer fitting 52. Channel spacer 62 extends coaxial along the length of inner shaft 24 from a proximal marker band 66 to approximately strain relief 22. Eight channels, 68A-68H, are spaced about its circumference as shown in FIG. 5. While eight channels are shown, any suitable number of channels may be chosen. Tubular spacer 64, also coaxial with inner shaft 24, extends from the proximal end of channel spacer 62 through hypotube shaft 48 to just distal of luer fitting 52. Hypotube shaft 48 acts as a support component for the proximal end of the inner shaft 24. Tubular spacer 64 is positioned within hypotube shaft 48 to decrease the annular space 70 between the hypotube shaft 48 and inner shaft 24 thus reducing the ability of the inner shaft 24 to deflect in a radial direction. Furthermore, tubular spacer 64 and channel spacer 62 support inner shaft 24 with respect to outer shaft 26 by eliminating slack when outer shaft 26 is moved with respect to inner shaft 24. Accordingly, this acts to increase the responsiveness of outer shaft 26 with respect to the movement of knob 18 such that there is one to one correlation between the amount of movement of knob 18 and outer shaft 26.

Catheter tip 72 is coupled to distal end 74 of inner shaft 24 approximate distal marker band 76. Tip 72 increases in diameter from inner shaft 24 to approximate the diameter of the outer shaft 26 at an intermediate section 78. Tip 72 then tapers in diameter to match guide wire port 80 at distal end of delivery system 10. This results in an atraumatic soft tip for smoothing the transition between guide wire 82, outer shaft 26 and guide wire port 80. Adjacent tip 72 is the stent receiving area 84 defined by the two marker bands, proximal marker band 66 and distal marker band 76. Inner shaft 24 may have a reduced cross section (not shown) to accommodate the stent in order to maintain a low profile for delivery system 10. Marker bands may also form a portion of a stop for the retained stent, such that the stent will remain in position on the inner shaft during the procedure as the outer shaft 26 is retracted during deployment. As seen in FIG. 4, proximal marker band 88 is positioned under an annular stop 90 surrounding inner shaft 24 and filling the proximal portion of stent receiving area 86 not filled by the stent. Likewise, marker band 92 is positioned on inner shaft 24 under the proximal end of catheter tip 94.

Stent 28 is a self expanding stent. A self expanding stent cut from a single Nickel-Titanium alloy hypodermic tube in a modular configuration such as that shown in FIGS. 6 and 7 may be used, although any suitable stent configuration may be used. In particular, the stent of FIG. 6 includes a series of tubular segments, one of which is designated 96, that consist of twelve crowns, one of which is designated 98, continuously joined in a sinusoidal pattern. This stent arrangement may be reduced for delivery in the configuration of crowns of the stent segments in contact with each other as shown in FIG. 8. In another stent configuration, the segments are staggered as shown in FIG. 7. In this, the segments alternative with different number of crowns. For example, the segment designated 102 preferably has twelve crowns and the segment designated 104 has fifteen crowns. This arrangement is advantageous for reducing the stent into the configuration shown in FIG. 9 where crowns 106a-106c have a radial position within the radial position of crowns 108a-i. While twelve and fifteen crowns are shown, any combination may be used depending upon the stent size and the amount of scaffolding desired.

To load the stent 28 into delivery system 10, stent 28 is radially reduced in size as known in the art by rolling the stent 28 into a reduced diameter and then placing the outer shaft 26 over stent 28. More particularly, as shown in the schematic of FIGS. 10-11, stent 110 in its expanded form is placed in a conventional roll down fixture 112. Stent 110 is preferably cooled, such as with liquid nitrogen, as it is mechanically rolled down. As it is rolled down, the roll down foil 112a is pulled with handle 112b causing stent 110 to be reduced in radial size against wedge 112c. Stent 110 is then pushed into a tubing 114 and the initial roll down is complete. The stent may then be loaded onto the delivery system 10 by placing it into inner shaft 24 and removing tubing 114 as outer shaft 26 is placed over the restrained stent. As shown in FIG. 8, crowns 116a-116l are compressed against each other in this first roll down configuration and each crown has the same radial position about the circumference of inner shaft 24.

Figure 9:
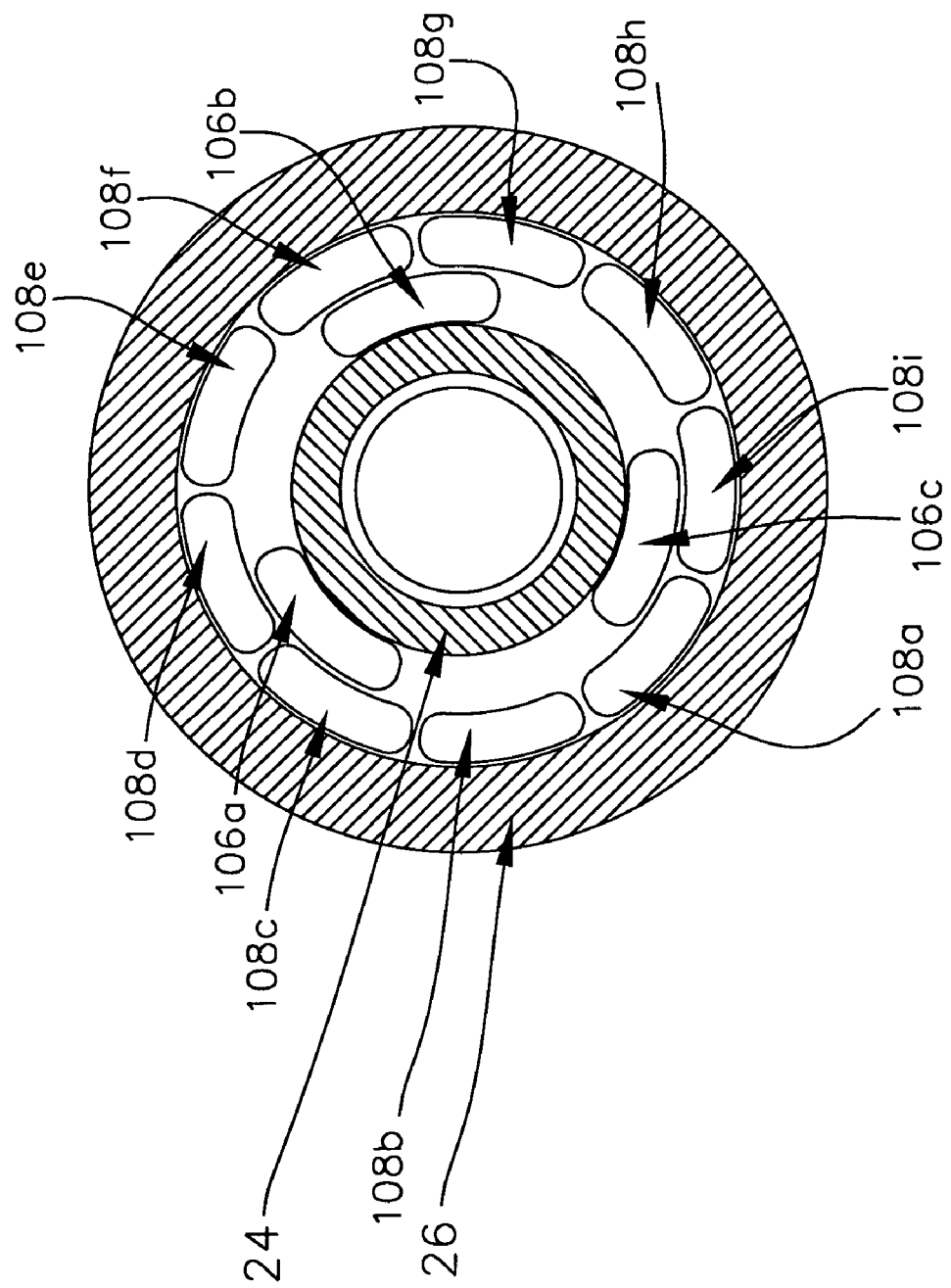
FIG. 9 is a cross sectional view of a reduced stent in a second configuration.
Figure 12:
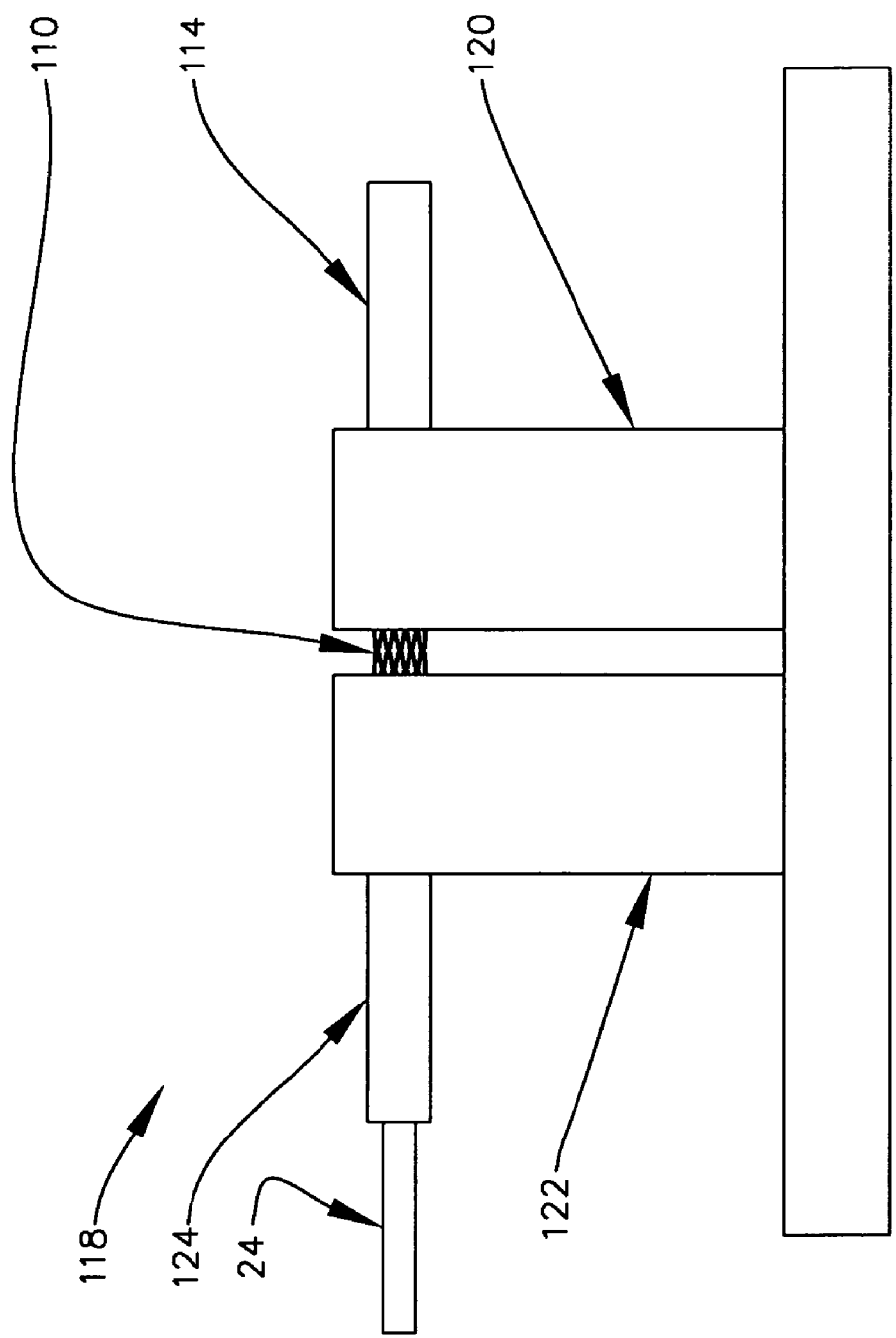
FIG. 12 is a schematic of a stent position in the final roll down fixture.

If it is desired to reduce stent 110 into a smaller diameter, the following procedure may be used. Secondary roll down fixture 118 (FIG. 12) contains a first block 120 and a second block 122. Tubing 114 and stent 110 are taken from the first roll down and placed in first block 120. Stent 110 is advanced out of tubing 114, and as it emerges, selected crowns of stent segments are pushed in, decreasing the diameter of the stent 110 and enabling it to be pushed into the smaller tubing 124 located in second block 122. Stent 110 is inserted into tubing 124 over the inner shaft 24 and positioned between marker bands 66 and 76. Preferably every fourth crown of the stent member is pushed down, and thus as shown in FIG. 9, the inner three crowns 106a-c have a shorter radial position about inner shaft 24 than the remaining crowns 108a-108i. While three crowns are shown pushed in for the stent having a staggered twelve and fifteen crown arrangement, the number of crowns depends upon the configuration of the stent and the desired reduced radial size of the stent. Once stent 110 is loading in tubing 124 and over inner shaft 24, distal end 126 of outer shaft 26 is placed over the stent 110. As outer shaft 26 is moved distally to cover the stent 110, it pushes tubing 124 off stent 110. Stent 110 can also be cooled, such as with liquid nitrogen, during this process to assist in the final roll down into outer shaft 26. As outer shaft 26 is moved distally over the shaft, knob 18 is also moved to its distal position in the longitudinal slot 16 and then rotated to sit in the transverse slot 20 to prevent unintended movement of outer shaft 26 and thus unintended deployment of stent. Once tubing 124 is removed, catheter tip 72 is mounted onto inner shaft 24.

Figure 13:
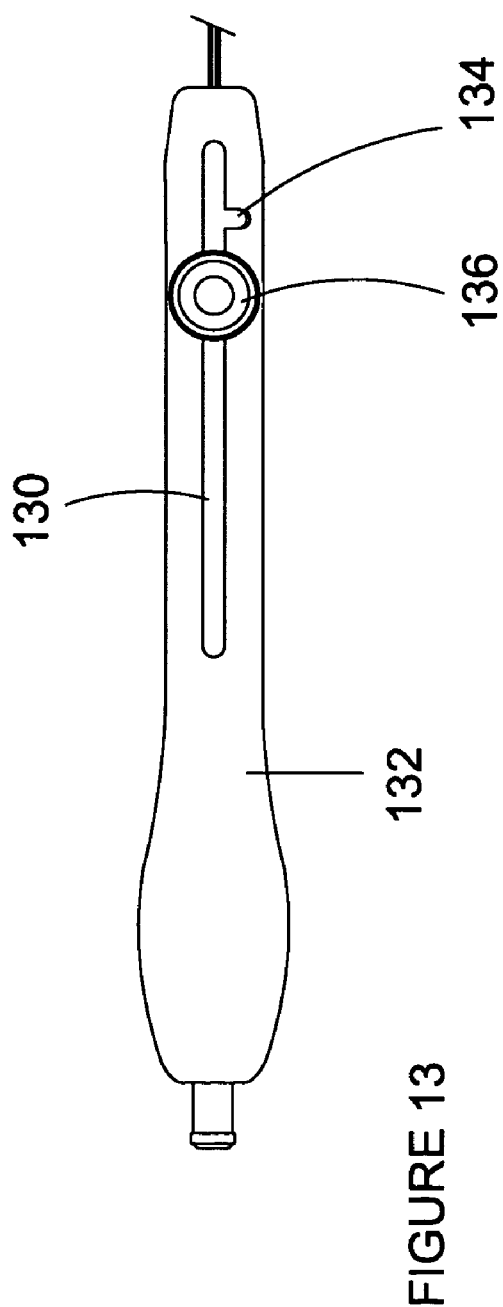
FIG. 13 is a side view of an alternative embodiment of the handle of the present invention.
Figure 14:
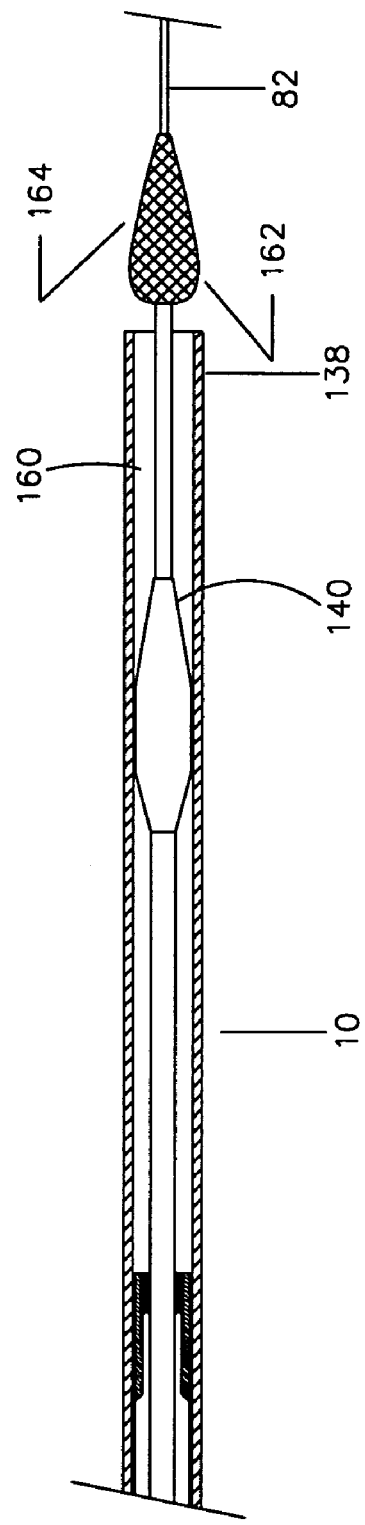
FIG. 14 is a cross-section view of the distal end of the present invention when used in conjunction with a distal protection device.

In an alternative embodiment shown in FIGS. 13 and 14, longitudinal slot 130 of the handle 132 extends distally past transverse slot 134. When knob 136 is slid in the distal direction past transverse slot 134, outer shaft distal portion 138 extends past catheter tip 140.

Figure 15:
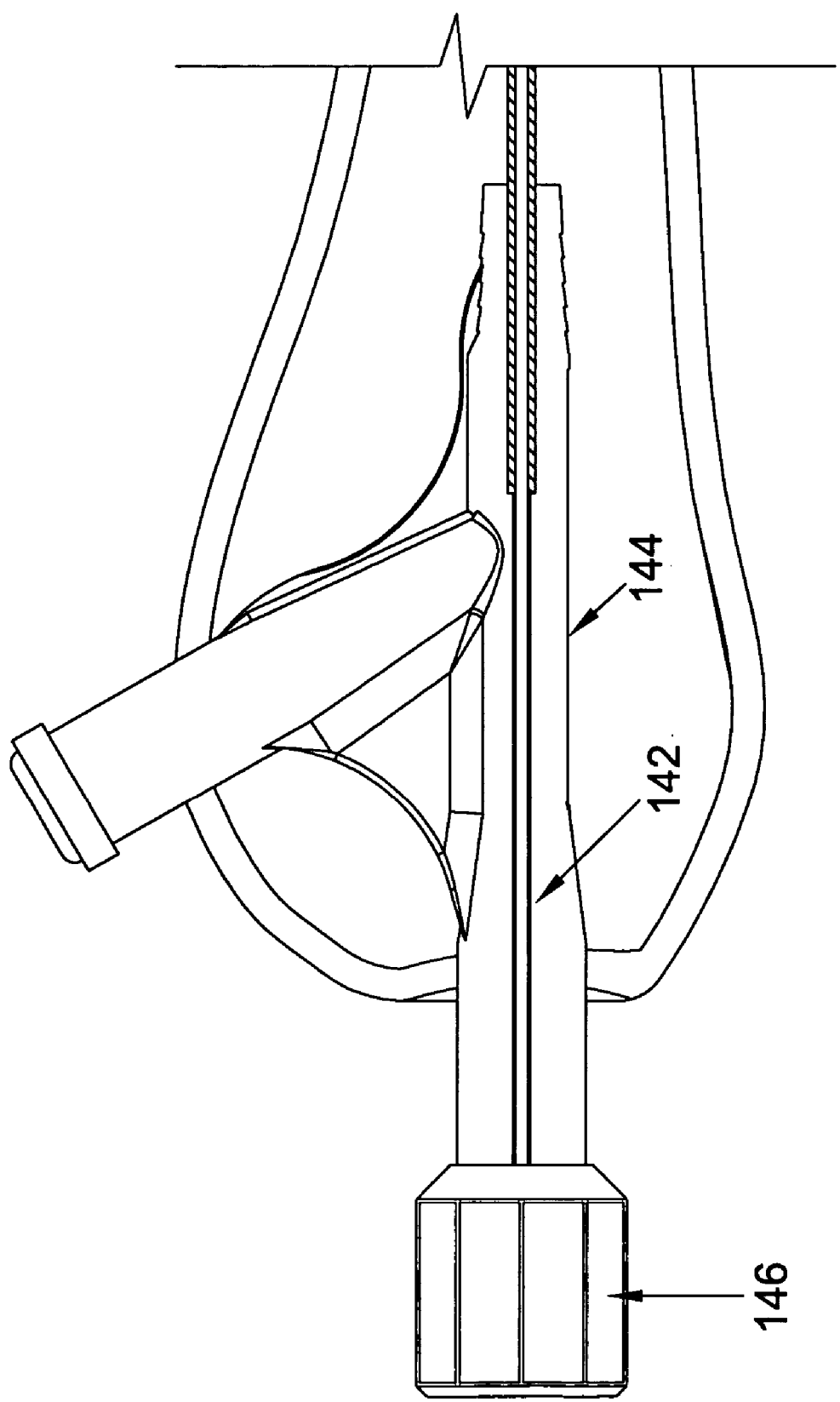
FIG. 15 is a cross-section view of another embodiment of the handle of the present invention.

A further embodiment is shown in FIG. 15. The inner shaft 142 extends past the luer fitting 144 to an annular knob 146 selectively coupled to the luer fitting 148.

When the knob 146 is released from the luer fitting 144 and moved proximally, inner shaft 142 will move proximally with respect to the outer shaft.

In use, the lumens of delivery system 10 are flushed via the luer fitting 44 with saline. An indwelling guide wire is inserted through the lumen of inner shaft 24. The catheter is inserted through the indwelling introducer or guiding catheter (or coupling member) (an outline of such a coupling member connected to an introducer is shown by the dashed lines 27). Valve relief 58 may be detached from the strain relief 22 and is positioned in the hemostatic valve or tuohy-borst coupler (not shown) which is then is tightened down around the valve relief 58. The stent 28 is advanced through the vessel and is positioned at the treatment site. Knob 18 is slowly slid with the operator's thumb or finger in a proximal direction along the slot 16 of handle 14 which the operator is holding. This causes outer shaft 26 to pull backwards in a proximal direction, slowly releasing the stent 28 in the vessel. The delivery system 10 is then removed from the vessel by holding the guide wire 82 in place and pulling back on the delivery system 10 in a proximal direction.

In the event that a distal protection device is being used during the vascular procedure, the present invention can be used for retrieving the distal protection device with the embodiments shown in FIGS. 13-15. After the stent is deployed, the delivery system of FIGS. 13 and 14 is advanced distally up to the basket 162 of the distal protection device 164. Knob 136 is slid forward in a distal direction with the operator's thumb or finger along longitudinal slot 130 past the transverse slot 134. This will result in outer shaft 138 extending past the tip 140, creating an area 160 between tip 140 and distal end of outer shaft 138 into which the distal protection device basket 162 can be drawn for removal. Both the delivery system 10 and the distal protection device 164 are then removed from the vessel by pulling the delivery system 10 and distal protection device 164 back in the proximal direction. With the embodiment of FIG. 15, knob 146 is released from the luer fitting 144 and moved proximally. Inner shaft 142 will also move in a proximal direction, creating an area 160 within the outer shaft 138 for accommodating a distal protection device.

The foregoing embodiments and examples are illustrative and are in no way intended to limit the scope of the claims set forth herein. For example. These and other alternatives are within the scope of the invention.

We claim:

1. A method for mounting on a delivery system a stent comprising a plurality of tubular segments connected in series, the method comprising:
    a) reducing the plurality of tubular segments to a first radial position, each of the tubular segments comprising a plurality of crowns located at the first radial position;

b) moving selected crowns from the first radial position to a second radial position, wherein the second radial position is less than the first radial position;

c) positioning the stent in the delivery system.

2. A method of claim 1 wherein positioning the stent in the delivery system comprises pulling the stent into the delivery system.

3. A method of claim 1 wherein reducing the stent to the first radial position comprises placing the stent in a roll down fixture, rolling the stent in the roll down fixture such that the crowns are in contact with each other, and placing the rolled down stent from the roll down fixture into a tubing.

4. A method of claim 1 and further including cooling the stent during steps a-c.

5. A method of claim 3 wherein the delivery system comprises an inner shaft and an outer retractable shaft, said method further comprising:

moving the stent over the inner shaft and adjacent at least one marker band; and placing the stent into the outer retractable sheath.

6. A method of claim 1 further comprising cutting the stent from a single hypodermic tube.

7. A method of claim 6 wherein the single hypodermic tube consists of a nickel-titanium alloy hypodermic tube.

8. A method of claim 7 wherein the stent is a self expanding stent.

9. A method of claim 1 wherein the tubular segments comprise a sinusoidal pattern.

10. A method of claim 1 wherein the tubular segments alternative with a different number of the crowns.

11. A method of claim 1 wherein a first tubular segment of the tubular segments consists of twelve crowns and a second tubular segment of the tubular segments consists of fifteen crowns.

12. A method of claim 1 wherein three crowns of the fifteen crowns of the second tubular segment are moved from the first radial position to the second radial position during the moving selected crowns from the first radial position to a second radial position.

13. A method of claim 1 wherein the moving selected crowns from the first radial position to a second radial position reduces the diameter of the stent.

* * * * *